US007195883B2

(12) United States Patent
Rosenquist et al.

(10) Patent No.: US 7,195,883 B2
(45) Date of Patent: Mar. 27, 2007

(54) SANDWICH ASSAYS FOR COLLAGEN FRAGMENTS (75) Inventors: Christian Rosenquist, Charlottenlund (DK); Per Qvist, Klampenborg (DK); Stephan Christgau, Gentofte (DK)

(73) Assignee: Osteometer Biotech A/S, Herlev (DK)

( * ) Notice: Subject to any disclaimer, the term of this patent is extended or adjusted under 35 U.S.C. 154(b) by 0 days.

(21) Appl. No.: 10/730,070

(22) Filed: Dec. 9, 2003

(65) Prior Publication Data

US 2004/0224375 A1 Nov. 11, 2004

Related U.S. Application Data (63) Continuation-in-part of application No. 09/319,539, filed as application No. PCT/EP97/06803 on Dec. 5, 1997, now Pat. No. 6,660,481.

(30) Foreign Application Priority Data

Dec. 9, 1996 (GB) ................. 9625559.1
Mar. 19, 1997 (GB) ................. 9705687.3

(51) Int. Cl.
*G01N 33/53* (2006.01)
(52) U.S. Cl. .................................... 435/7.94
(58) Field of Classification Search ........... 435/7.1, 435/4, 7.94
See application file for complete search history.

(56) References Cited

U.S. PATENT DOCUMENTS 5,320,970 A * 6/1994 Eyre ..................... 436/536

6,010,863 A * 1/2000 Te Koppele et al. ......... 435/7.1
6,107,047 A * 8/2000 Fledelius et al. ........... 435/7.1
6,300,083 B1 * 10/2001 Fledelius et al. ........... 435/7.1
6,660,481 B2 * 12/2003 Rosenquist et al. ......... 435/7.1
2004/0224375 A1* 11/2004 Rosenquist et al. ........ 435/7.93

FOREIGN PATENT DOCUMENTS

| DK | WO 95/08115 | * | 3/1995 |
| GB | WO 98/35235 | * | 8/1998 |
| JP | 9-21803 | * | 1/1997 |

OTHER PUBLICATIONS

Kobayashi T. et al. Synovial Fluid Concentrations of the C Propeptide of Type II Collagen Correlate with Body Mass Index in Primary Knee Osteoarthritis. Annals of the Rheumatic Diseases Aug. 1997. 56(8)500-503.*
Shinmei M. et al. Joint Fluid Carboxy Terminal Type II Procollagen Peptide as a Marker of Cartilage Collagen Biosynthesis. Osteoarthritis and Cartilage 1993 vol. 1, 121-128.*
Dusemund B. et al. Double Antibody Enzyme Lined Immunosorbent Microassay for Quantification of Collagen Types I an II. J of Immunological Methods May 1982. 50(3)255-268.*

* cited by examiner

*Primary Examiner*—Ralph Gitomer
(74) *Attorney, Agent, or Firm*—Gregory Butler, Esq.; Edwards Angell Palmer & Dodge, LLP (57) ABSTRACT 0Type II collagen degradation is measurable using a sandwich immunoassay in which a single antibody specific for the amino acid sequence EKGPDP is used to form each side of antibody-collagen fragment-antibody sandwich complexes and the amount of said complexes is measured.

4 Claims, 3 Drawing Sheets

Fig 4 ic acid sequences of human type III collagen, human pro a1(II) collagen, and the entire prepro a1(III) chain of human type III collagen and corresponding cDNA clones

SANDWICH ASSAYS FOR COLLAGEN FRAGMENTS

1. CROSS REFERENCE TO RELATED APPLICATIONS

This application is a continuation-in-part of U.S. application Ser. No. 09/319,539, filed Jun. 8, 1999 now U.S. Pat. No. 6,660,481, which is a continuation of the national stage designation of PCT/EP97/06803, filed Dec. 5, 1997, the disclosures of which are incorporated herein in their entirety

2. FIELD OF THE INVENTION

The present invention relates to assays for collagen fragments in body fluids.

3. BACKGROUND

3.1. Collagens and Disorders of Collagen Metabolism

Osteoporosis is the most common bone disease in humans. Primary osteoporosis, accompanied by increased susceptibility to fractures, results from a progressive reduction in skeletal bone mass. It is estimated to affect 15–20 million individuals in the USA alone. Its basis is an age-dependant imbalance in bone remodelling, i.e. in the rates of formation and resorption of bone tissue.

In the USA about 1.2 million osteoporosis-related fractures occur in the elderly each year including about 538,000 compression fractures of the spine, about 227,000 hip fractures and a substantial number of early fractured peripheral bones. Between 12 and 20% of the hip fractures are fatal because they cause severe trauma and bleeding, and half of the surviving patients require nursing home care. Total costs from osteoporosis-related injuries now amount to at least $10 billion annually in the USA (Riggs, New England Journal of Medicine, 327:620–627 (1992)).

Osteoporosis is most common in postmenopausal women who, on average, lose 15% of their bone mass in the 10 years after menopause. This disease also occurs in men as they get older and in young amenorrheic women athletes. Despite the major, and growing, social and economic consequences of osteoporosis, the availability of reliable assays for measuring bone resorption rates in patients or in healthy subjects is very limited. Other disorders entailing (and correlated with) abnormalities in collagen metabolism include Paget's disease, Marfan's syndrome, osteogenesis imperfecta, neoplastic growth in collagenous tissue, dwarfism, rheumatoid arthritis, osteo-arthritis and vasculitis syndrome.

Three known classes of human collagen have been described to date. The Class I collagens, subdivided into types I, II, III, V, and XI, are known to form fibrils.

The amino-acid sequence of type I–III (to the extent it has been elucidated) is given in Appendix A of WO 95/08115.

Collagen type I accounts for more than 90% of the organic matrix of bone. Therefore, in principle, it is possible to estimate the rate of bone resorption by monitoring the degradation of collagen type I. Likewise, a number of other disease states involving connective tissue can be monitored by determining the degradation of collagen. Examples are collagen type II degradation associated with rheumatoid arthritis and osteo-arthritis and collagen type III degradation in vasculitis syndrome.

Amino acid sequences of human type III collagen, human pro a1(II) collagen, and the entire prepro a1(III) chain of human type III collagen and corresponding cDNA clones have been investigated and determined by several groups of researchers; see Loil et al., Nucleic Acid Research 12:9383–9394 (1984); Sangiorgi et al., Nucleic Acids Research, 13:2207–2225 (1985); Baldwin et al., Biochem J., 262:521–528 (1989); and Ala-Kokko et al., Biochem. J., 260:509–516 (1989).

Type I, II, and III collagens are all formed in the organism as procollagen molecules, comprising N-terminal and C-terminal propeptide sequences, which are attached to the core collagen molecules. After removal of the pro-peptides, which occurs naturally in vivo during collagen synthesis, the remaining core of the collagen molecules consists largely of a triple-helical domain having terminal telopeptide sequences which are non-triple-helical. These telopeptide sequences have an important function as sites of intermolecular cross-linking of collagen fibrils extra-celluarly. The alpha-helical region also includes cross-linkable sites.

Intermolecular cross-links provide collagen fibrils with biomechanical stability. The formation of these cross-links is initiated by modification of lysine and hydroxylysine residues to the corresponding aldehydes. Several of these residues located on adjacent chains of collagen will spontaneously form different intermolecular cross-links. The exact position of the sites for cross-linking on collagen telopeptides and from the helical region has been previously described. See, for example, Kühn, K., in Immunochemistry of the extracellular matrix, 1:1–29, CRC Press, Inc., Boca Raton, Fla. (1982), Eyre, D. R., Ann. Rev. Biochem., 53:717–48 (1984) or U.S. Pat. Nos. 5,140,103 and 5,455,179. Furthermore, the amino acid sequences of some potential sites for cross-linking in type I, II, and III collagen are given in Table 1 below.

The fibrous proteins, collagen and elastin, are cross-linked by a unique mechanism based on aldehyde formation from lysine or hydroxylysine side chains. Four homologous loci of cross-linking are evident in molecules of type I, II and III collagens (for review see Kühn, K., in Immunochemistry of the extracellular matrix, 1:1–29 (1982)). Two are aldehyde sites, one in each telopeptide region. The other two sites are hydroxylysine symmetrically placed at about 90 residues from each end of the molecule. When collagen molecules pack into fibrils, these latter sites in the helical region align and react with telopeptide aldehydes in adjacent molecules. There is now strong evidence that 3-hydroxypyridinium residues are the mature cross-link coming from hydroxylysine-derived aldehydes. The mature cross-linking residues of the other pathway, i.e. from aldehyde formation of lysine residues, are however, still unknown.

As illustrated by formula in EP-0394296 discussed below, the two 3-hydroxypyridinium cross-links have been found to be hydroxylysyl pyridinoline (also known simply as "pyridinoline") and lysyl pyridinoline (also known as "deoxypyridinoline"). These cross-linking compounds are naturally fluorescent. Some hydroxylysyl pyridinoline cross-link are found to be glycosylated as discussed for instance in EP-A-0424428.

However, as described in Last et al, Int. J. Biochem. Vol. 22, No. 6, pp 559–564, 1990 other crosslinks occur naturally in collagen.

3.2. Prior Art Assays for Collagen Degradation

In the past, assays have been developed for monitoring degradation of collagen in vivo by measuring various biochemical markers, some of which have been degradation products of collagen.

For example, hydroxyproline, an amino acid largely restricted to collagen, and the principal structural protein in bone and all other connective tissues, is excreted in urine. Its excretion rate is known to be increased in certain conditions, notably Paget's disease, a metabolic bone disorder in which bone turnover is greatly increased, as discussed further below.

For this reason, urinary hydroxyproline has been used extensively as an amino acid marker for collagen degradation; Singer, F. R. et al., Metabolic Bone Disease, Vol. II (eds. Avioli, L. V., and Kane, S. M.), 489–575 (1978), Academic Press, New York.

U.S. Pat. No. 3,600,132 discloses a process for the determination of hydroxyproline in body fluids such as serum, urine, lumbar fluid and other intercellular fluids in order to monitor deviations in collagen metabolism. The Patent states that hydroxyproline correlates with increased collagen anabolism or catabolism associated with pathological conditions such as Paget's disease, Marfan's syndrome, osteogenesis imperfecta, neoplastic growth in collagen tissues and in various forms of dwarfism.

Bone resorption associated with Paget's disease has also been monitored by measuring small peptides containing hydroxyproline, which are excreted in the urine following degradation of bone collagen; Russell et al., Metab. Bone Dis. and Rel. Res. 4 and 5, 2250262 (1981), and Singer, F. R., et al., supra.

In the case of Paget's disease, the increased urinary hydroxyproline probably comes largely from bone degradation; hydroxyproline, however, generally cannot be used as a specific index for bone degradation. Much of the hydroxyproline in urine may come from new collagen synthesis (considerable amounts, of the newly made protein are degraded and excreted without ever becoming incorporated into tissue fabric), and from turnover of certain blood proteins as well as other proteins that contain hydroxyproline.

Furthermore, about 80% of the free hydroxyproline derived from protein degradation is metabolised in the liver and never appears in the urine. Kiviriko, K. I., Int. Rev. Connect. Tissue Res. 5:93 (1970), and Weiss, P. H. and Klein, L., J. Clin. Invest. 48:1 (1969). Hydroxyproline is a good marker for osteoporosis as it is specific for collagen in bones even if it is not specific for bone resorption, but it is trouble-some to handle.

Hydroxylysine and its glycoside derivatives, both peculiar to collagenous proteins, have been considered to be more accurate than hydroxyproline as markers of collagen degradation. However, for the same reasons described above for hydroxyproline, hydroxylysine and its glycosides are probably equally non-specific markers of bone resorption; Krane, S. M. and Simon, L. S., Develop. Biochem. 22:185 (1981).

Other researchers have measured the cross-linking compound 3-hydroxypyridinium in urine as an index of collagen degradation in joint diseases. See, for background and as examples, Wu and Eyre, Biochemistry, 23:1850 (1984): Black et al., Annals of the Rheumatic Diseases, 45:969–973 (1986); and Seibel et al., The Journal of Dermatology, 16:964 (1989). In contrast to the present invention, these prior researchers have hydrolysed peptides from body fluids and then looked for the presence of free 3-hydroxypyridinium residues.

Assays for determination of the degradation of type I, II, and III collagen are disclosed in EP-0394296 and U.S. Pat. No. 4,973,666 and U.S. Pat. No. 5,140,103. However, these Patents are restricted to collagen fragments containing the cross-linker 3-hydroxypyridinium. Furthermore, the above mentioned assays require tedious and complicated purifications from urine of collagen fragments containing 3-hydroxypyridinium to be used for the production of antibodies and for antigens in the assays.

Until recently very few clinical data using the approach described in U.S. Pat. No. 4,973,666 and U.S. Pat. No. 5,140,103 are available. Particularly, no data concerning the correlation between the urinary concentration (as determined by methods described in the above mentioned patents) of 3-hydroxypyridinium containing telopeptides of type I collagen and the actual bone loss (as determined by repeated measurements by bone densitometry) had been published. Very recently however McClung et al (JBMR (1996) 11:129) have concluded that results from the commercial NTx assay based on these Patents do not correlate to bone loss. More particularly, NTx did not correlate to bone loss in the normal population and also failed to predict bone changes in response to therapy. Gertz et al (JBMR (1994) 9(2): 135–142) have reported no significant correlation between baseline NTx measurements and bone loss and no significant correlation between change in NTx and change in bone loss during anti-resorptive therapy.

Garnero et al (JBMR (1996) 11(10): 1531–1537) have reported that NTx was found not be predictive of hip fracture whilst other biochemical markers were associated with an approximately 100 percent increased risk of hip fracture.

The presence of 3-hydroxypyridinium containing telopeptides in urine requires the proper formation in bone tissue of this specific cross-linking structure at various times before the bone resorbing process. Very little information on these processes is available and it would be desirable to avoid this dependence of the correct formation of the cross-linking structure.

GB Patent Application No. 2205643 reports that the degradation of type III collagen in the body can be quantitatively determined by measuring the concentration of an N-terminal telopeptide from type III collagen in a body fluid. This method uses antibodies generated to N-terminal telopeptides released by bacterial collagenase degradation of type III collagen, said telopeptides being labelled and used in the assay.

Schrater-Kermani et al., Immunol. Invest. 19:475–491 (1990) describe immunological measurement systems based on CNBr fragments of collagen type I and II. Use is made of pepsin-solubilised collagen, leaving the telopeptides in the tissue (cf. the above mentioned GB Patent Application No. 2205643). There is therefore no conformity between the fragments and the antibodies raised therefrom. Further, the reference only describes measurements on extracted tissue samples.

The development of a monoclonal antibody raised against pepsin-solubilised type I collagen is described in Werkmeister et al., Eur. J. Biochem. 1987:439–443 (1990). The antibody is used for immunohistochemical staining of tissue segments and for measuring the collagen content in cell cultures. The measurements are not carried out on body fluids.

EP Patent Application No. 0505210 describes the development of antibody reagents by immunisation with purified cross-linked C-terminal telopeptides from type I collagen. The immunogen is prepared by solubilising human bone collagen with bacterial collagenase. The antibodies thus prepared are able to react with both cross-linked and non-cross-linked telopeptides, and cross-linkers other than pyridinoline.

There are a number of reports indicating that collagen degradation can be measured by quantitating certain procollagen peptides. Propeptides are distinguished from telopeptides and alpha-helical region of the collagen core by their location in the procollagen molecule and the timing of their cleavage in vivo; see U.S. Pat. No. 4,504,587; U.S. Pat. No. 4,312,853; Pierard et al., Analytical Biochemistry 141: 127–136 (1984); Niemela, Clin. Chem. 31/8:1301–1304 (1985); and Rohde et al., European Journal of Clinical Investigation, 9:451–459 (1979).

EP Patent Application No. 0298210 and No. 0339443 both describe immunological determination of procollagen peptide type III and fragments thereof. Further, a method based on the measurement of procollagen is disclosed in EP Patent Application No. 0465104.

The use of synthetic peptides with sequences derived from type IX collagen for the development of immunological reagents is disclosed in PCT Patent Application No. WO 90/08195. Likewise the application describes the use of the antibodies thus produced for the determination of type IX collagen fragments in body fluids. U.S. Pat. No. 4,778,768 relates to a method of determining changes occurring in articular cartilage involving quantifying proteoglycan monomers or antigenic fragments thereof in a synovial fluid sample.

Dodge, J. Clin Invest 83:647–661 (1981) discloses methods for analysing type II collagen degradation utilising a polyclonal antiserum that specifically reacts with unwound alpha-chains and cyanogen bromide-derived peptides of human and bovine type II collagens. The degradation products of collagen were not detected in a body fluid, but histochemically by staining of cell cultures, i.e. by "in situ" detection.

WO 94/03813 describes a competitive immunoassay for detecting collagen or collagen fragments in a sample wherein a binding partner containing a synthetic linear peptide corresponding to the non-helical C-terminal or N-terminal domain of collagen is incubated with an antibody to the linear synthetic peptide and the sample, and wherein the binding of the antibody to the binding partner is determined.

WO 95/08115 relates to assay methods in which collagen fragments in a body fluid are determined by reaction with an antibody which is reactive with a synthetic peptide. The assay may be a competition assay in which the sample and such a peptide compete for an antibody, possibly a polyclonal antibody raised against fragments of collagen obtained by collagenase degradation of collagen. Alternatively, it may be an assay in which an antibody, possibly a monoclonal anti-body, is used which has been raised against such a synthetic peptide.

As disclosed in WO 91/08478, one particular type of peptide fragment found in body fluid, particularly urine, is of the formula:

Formula 1

In the above formula, K-K-K is disclosed as representing a hydroxypyridinium cross-link but in fact it may be any naturally occurring cross-link and specifically any of those discussed in the above referenced paper of Last et al. As further discussed below, larger peptide fragments including the above smaller fragment are also disclosed in this document.

A proportion of the "peptide" fragments in body fluid are related to peptides of equivalent amino acid sequence, e.g. peptides of formula 1, by the isomerisation of aspartic acid in the formula to isoaspartic acid. We put "peptides" in quotes here as of course the isomerisation means that these species are no longer properly regarded as being peptides.

The isomerisation of proteins containing aspartic acid has been reported previously to be a spontaneous reaction occurring under physiological conditions.

See for instance Brennan et al Protein Science 1993, 2, 331–338, Galletti et al, Biochem. J. 1995, 306, 313–325, Lowenson et al, Blood Cells 1988, 14, 103–117 and Oliya et al, Pharmaceutical Research, Vol. 11, No. 5, 1994, p. 751.

The isomerisation has the effect of transferring that part of the peptide chain which runs downstream of the aspartic acid residue in the carboxy terminus direction from the alpha carboxylic acid of the aspartic acid to which it is bonded via a peptide bond in the normal protein to the side chain carboxylic acid in a non-peptide amide bond, as shown below:

The non-peptide bonded aspartic acid residue is termed "isoaspartic acid" or β-aspartic acid (βD)

Similar isomerisation can occur in proteins containing asparagine residues (i.e. with —NH2 instead of —OH in the starting protein in the above reaction scheme).

The above discovery indicates that this isomerisation also occurs in bone tissue and the extent of isomerisation is expected therefore to be marker for the age of the bone tissue concerned.

Furthermore, the presence amongst such bone peptide fragments of the isomerised peptides provides confirmation that the fragments indeed derive from bone degradation and not some other source such as the degradation of newly formed collagen never incorporated into bone.

J. Macek and M. Adam "Determination of collagen degradation products in human urine", Z. Rheumatol. 46:237–240 (1987) reports the presence of pyridinoline containing collagen cross-linked peptides in urine having a molecular weight above 10,000 but provides no sequence information relating to the peptide chains present or the collagen type to which the fragments belong.

As mentioned above WO91/08478 discloses that a number of fragments of type 1 collagen can be found in urine. These include a pyridinium crosslink, which may be hydroxylysyl pyridinoline or lysyl pyridinoline. Attached to the crosslink are peptide chains of defined sequence derived from the collagen molecule. The crosslink has three points at which it may bear peptide chains. The fragment of Formula 1 above (Formula VI in WO91/08478) bears two chains, each having the sequence EKAHDGGR. Two other fragments are described in WO91/08748 which each have a third chain, that shown in Formula IV of that specification being 7 amino acids longer than that in Formula V, but otherwise of the same sequence. The amino-acid sequence of the chains of type 1 collagen has been published elsewhere as described above, as has the location of the trivalent crosslinks between the collagen molecules. The third chain depicted in the said Formulae IC and V of WO91/08748 does not correspond to that of any collagen chain at the location of the crosslink and is believed to be an error, possibly caused by an artefact of the isolation procedure used.

The only fragment for which a credible formula has been given is there for that of Formula VI (equivalent to Formula 1 herein) having two identical peptide chains.

DE-A-4225038 discloses sandwich assays for collagen breakdown products in body fluids. Antibodies are to be produced by immunisation with haptens containing a linear sequence of amino acids. One proposed sequence is FDF-SFLP (SEQ ID No.2) and another is PPQEKAHDGGR (SEQ ID No.3), although these were not suggested for use in combination to make two antibodies for use in the same sandwich assay. Indeed although the sequence PPQE-KAHDGGR is given, no antibodies made against it are specifically described and therefore no disclosure is provided of their actual utility and properties. The only specific sandwich assay described combines an antibody against the C-terminal sequence FDFSFLP with one against the sequence GMKGHRGF (SEQ ID No.4) (from the helical region crosslink site).

However, DE-A-4225038 asserts that there is a close correlation between results obtained using an assay based on the sequence FDFSFLP and a commercial assay known as the ICTP assay. It has been shown however that the ICTP assay in serum does not appear to reflect bone resorption in that the results it produces do not successfully track the effect of therapeutic treatment (Hassager et al. Calcif. Tissue. Int. (1994) 54:40–33). This of course would imply that the population of reflect bone resorption in a useful way.

We have now established that body fluids do in fact contain larger collagen fragments containing not only the sequence EKAHDGGR but also further amino acid residues. These may be present in a third chain attached to the crosslink with two chains incorporating the sequence EKAHDGGR and/or as extensions of N-amino terminal direction of the sequence EKAHDGGR of one or both of the two chains containing that sequence.

We have further established that surprisingly it is possible to obtain binding of two distinct antibodies to a single collagen degradation fragment where both antibodies are specific for an epitope in the sequence EKAHDGGR or a variant of it.

4. SUMMARY OF THE INVENTION

The present invention encompasses methods of measurement of the rate of type I collagen resorption comprising measuring in a sample (e.g. a body fluid) the amount of a population of collagen fragments by a sandwich assay using a first antibody reactive with a first epitope located in the collagen amino acid sequence EKAHDGGR or in isomerised and/or racemised variants thereof and a second antibody reactive with a second collagen epitope located in said fragments.

In an illustrative example, the body fluid on which the assay is conducted is other than urine.

In another illustrative example, said epitope is treated in the sequence AHDGGR or a said variant of it (SEQ ID No.7).

Optionally, said second epitope is located in the N-amino terminal direction with respect to said first epitope in the same or a different collagen chain. If so, it may include at least a part of the amino acid sequence FDFSF.

The assay may therefore be based on the sequence FDF-SFLP and on the sequence EKAHDGGR.

In another illustrative example, the molecular weight of fragments detected in the assay exceeds 1500 Da, more preferably 5000 Da. However, the molecular weight of the fragments may exceed 10000 Da or even 25000 Da.

Said second collagen epitope is preferably also located in the amino acid sequence EKAHDGGR or in isomerised and/or racemised variants thereof. Each said epitope is therefore preferably present in a respective amino acid chain attached to a crosslink. Preferably each said epitope is located in the amino acid sequence EKAH-βD-GGR (SEQ ID No.5). The antibodies employed are preferably in each case a monoclonal antibody raised against a peptide analogue containing the amino acid sequence EKAH-βD-GGR.

The invention encompasses sandwich assays for collagen degradation products in which antibodies of essentially identical specificity are used on both sides of the sandwich, e.g. antibodies each specific for the same amino acid sequence within the C-or N-telopeptide region of collagen, especially collagen type I or type II or type III. For an assay of type II collagen degradation products in body fluids it is preferred that the antibodies used on each side of the sandwich in the assay are reactive specifically with the epitope defined by or in the sequence EKGPDP (SEQ ID No:8). The antibodies may be monoclonal or polyclonal. One of the antibodies may be monoclonal and the other polyclonal, but the use of two monoclonal antibodies of the same specificity or of the same monoclonal antibody on each side of the sandwich is preferred.

One or both antibodies may be mAb1H11 described in WO96/36645 or may have similar specificity thereto, i.e. specificity for an epitope contained in the metabolite with which said in mAb1H11 is immunologically reactive.

In a further aspect, the invention encompasses a method of measurement of the concentration of collagen degradation products in a sample comprising conducting a sandwich assay using first and second immunological binding partners (which may be the same or different) each immunologically reactive with an epitope in an N-terminal telopeptide fragment produced upon collagen degradation in vivo. Such N-terminal fragments may be as described in U.S. Pat. No. 5,455,179 and one or both of the antibodies may be mAb1H11 or have equivalent specificity. The second antibody may be reactive with an eptiope containing amino acid sequence crosslinked in collagen type I degradation products with the mAb1H11 epitope sequence. Accordingly, the fragments may be Type I collagen fragments. Preferably, at least one of the antibodies in specific for an epitope containing an isomerised aspartic acid or asparagine residue.

5. BRIEF DESCRIPTION OF THE FIGURES

The accompanying drawings show results obtained according to methods of the invention.

5. DETAILED DESCRIPTION OF THE INVENTION

5.1 Preparation of Antibodies

The preparation of antibodies reactive with the sequence EKAHDGGR has been described in WO95/08115, including methods for the preparation of monoclonal antibodies. As described in WO96/30765 this sequence may be isomerised at the aspartate residue such that this is linked to the following glycine by its β carboxylic acid group. The preparation of monoclonal antibodies to that isomerised sequence is taught there. As described in PCT/EP97/04372 either the normal sequence or the isomerised sequence may become racemised at the aspartate residue so that one or both chains contains a D-aspartic acid residue either bonded normally or via the β carboxylic acid group. The production of monoclonal antibodies to the normal or iso-D forms of the sequence may be carried out by processes analogous to those described in WO95/08115 or in WO96/30765. Any of these monoclonal antibodies may be used in the present invention as either or both of the two antibodies, which may have identical specificity. Generally, one antibody will be coupled to a substrate, e.g. a solid or particulate support, and the other will be coupled to a direct or indirect label.

The second antibody for use in the invention may be a monoclonal antibody produced by immunisation with bacterial collagenase treated collagen (CTC) followed by selection for antibodies reactive with a selected peptide sequence such as that set out below taken from the sequence of the collagen molecule upstream (i.e. in the N-terminal direction) from the sequence EKAHDGGR. Preferably in this case, the sequence is one which embraces the immunogenic sequence FDFSFL. A preferred peptide for this purpose is one that contains the sequence FDFSFL plus additional amino acids at one or more preferably both ends such as CSAGFDFS-FLPQPPQE (SEQ ID No.6). Alternatively, immunisation may be carried out with the peptide itself conjugated to a suitable carrier according to known techniques.

Where both epitopes are contained in the same amino acid sequence, e.g. EKAHDGGR or its variants, both antibodies may be the same or may be raised in the same way.

The methods of preparation of monoclonal antibodies are well known in the art. For example, see Campbell, A. M., Laboratory Techniques in Biochemistry and Molecular Biology, Vol. 12 (1986). It is possible to produce antibodies to synthetic peptides or their isomerised or racemised variants by immunisation. However, because of the relatively small molecular weight of these compounds it is preferred that the hapten be conjugated to a carrier molecule. Suitable carrier molecules include, but are not limited to, bovine serum albumin, thyroglobulin, ovalbumin, tetanus toxoid, and keyhole limpet haemocyanin. The preferred carrier is bovine serum albumin. To present the hapten in its most immunogenic form to the antibody producing cells of the immunised animal a number of alternative coupling protocols can be used. Suitable procedures include, but are not limited to, glutaraldehyde, carbodiimide, and periodate. Preferred binding agents are glutaraldehyde and carbodiimide.

The preparation of antibodies may also be carried out by conventional techniques including immunisation with collagen fragments which may contain natural isomerisation or with an adjuvant before injection. Examples of adjuvants include, but are not limited to, aluminium hydroxide, Freund's adjuvant, and immune-stimulating complexes (IS-COMs). ISCOMs can be made according to the method described by Morein, B. et al., Nature 308:457–460 (1984).

Either monoclonal or polyclonal antibodies to the hapten-carrier molecule can be produced. For the production of monoclonal antibodies it is preferred that mice are immunised. Spleen cells from the immunised mouse are harvested, homogenised, and thereafter fused with cancer cells in the presence of polyethylene glycol to produce a cell hybrid which produces monoclonal antibodies specific for isomerised peptide fragments derived from collagen. Suitable cancer cells include, but are not limited to, myeloma, hepatoma, carcinoma, and sarcoma cells. Detailed descriptions of the production of monoclonal antibodies are provided in Goding, J. W., in Monoclonal Antibodies: Principles and Practice, (1986). A preferred preliminary screening protocol comprises the use of synthetic peptides or isomerised or racemised peptide analogues conjugated to a carrier and coated on to the solid surface of a microtitre plate.

For the preparation of polyclonal antibodies, different animal species can be immunised. Suitable species include, but are not limited to, chicken, rabbit and goat. Chicken and rabbit are preferred.

Antibodies so produced may be screened for suitability for use according to the invention by testing for reactivity with a synthetic peptide or peptide analogue of appropriate sequence.

Antibody fragments are prepared by methods known in the art (see E. Ishikawa. Journal of Immunoassay 3:209–327 (1983)).

It is possible to omit (or add) one or more amino acid residues from (or to) the crosslink site sequences without substantial loss of the ability to raise antibodies recognising the corresponding native collagen fragment. It is possible to use longer collagen fragments and/or chimeric peptide analogues to raise the antibodies. It is possible to make substitution of one or more amino acids which are not critical for antibody recognition.

The preparation of synthetic peptides and peptide analogues may be performed according to procedures well known in the art, e.g. by solid-phase peptide synthesis techniques commonly described as "Merrifield synthesis". Also classical solution phase techniques may be used.

The sandwich assay according to the present invention may be conducted according to any of the known sandwich assay formats. These include formats in which one antibody is provided on a solid support and the other is labelled in one of many known ways including the use of radio-isotope labels. The antibodies and revealing reagents for the conduct of an immunoassay using standard detection protocols, for example radioisotope labelling, fluorescent labelling or ELISA, may conveniently be supplied as kits which include the necessary components and instructions for the assay. In one embodiment of the invention such a kit includes a microtitre plate coated with a relevant antibody, standard solutions for preparation of standard curve, a body fluid (e.g. serum) control for quality testing of the analytical run, a second antibody reactive with a second epitope in fragments to be detected conjugated to an enzyme such as horse radish peroxidase or otherwise labelled, a substrate solution, a stopping solution, a washing buffer and an instruction manual.

Both antibodies may be bound to a micro-particle, e.g. in a latex emulsion, so that binding of the antibodies to the target produces an agglutination which can be observed by known techniques such as light transmission or scattering measurements.

However, the two antibodies can be mixed with the sample before one of the antibodies is bound to a capture substrate such as a microtitre plate or other form of solid support such as micro-beads. For such use one antibody may be coupled to a capture moiety which has affinity for and can be captured on a capture substrate. It is preferred that the other antibody is coupled to a direct or indirect label.

The capture moiety may for instance be biotin. Biotinylated antibodies may be captured on a capture substrate bearing avidin or streptavidin.

The use of such a format is particularly suitable where each antibody has the same or an overlapping specificity, there being two identical or mutually interfering epitopes in each of the collagen degradation fragments to be detected. Addition of the target fragments to either one of the antibodies separately may result in both epitopes being bound by the first antibody, so that the second antibody when added does not bind. This may occur even when the first antibody is immobilised on a solid surface. If both antibodies are mixed with the target fragments at the same time, sandwiches containing the first antibody, the target fragment and the second antibody can be formed. These may then be captured to a capture substrate by the capture moiety present on one antibody and the captured sandwich can then be detected via the label of the other antibody.

Accordingly the invention provides in a separate aspect a method of conducting a sandwich assay comprising:

mixing a target antigen containing at least two antigenically similar epitopes with a first antibody reactive with both said epitopes, which first antibody is coupled to a capture moiety and with a second antibody reactive with both said epitopes, which second antibody is coupled to a label, so as to form a first antibody-target antigen-second antibody sandwich, capturing said sandwich to a capture substrate having an affinity for said capture moiety of said first antigen, and detecting the capture of said sandwich by detection of the label of the second antibody.

Since immunoassays can be constructed using antibodies specific for synthetic isomerised and/or racemised peptide analogues, the ratios of the corresponding collagen fragment sequences in an appropriate biological fluid can be determined as well as their individual levels and their total. Thus, the assay can be designed to include antibodies which will result in determination of fragments containing several isoaspartic acid containing and/or racemised peptide analogues and optionally the native peptide sequences or determination of a single isoaspartic acid containing and/or racemised peptide analogue sequence, or any desired combination thereof.

In addition to the use of the herein specified peptides as indicators of bone resorption, bone metabolic balance is advantageously determined by the substantially simultaneous determination of a marker of the formation of bone in the same or other appropriate biological fluid form the same individual. "Substantially simultaneous" means the same day, preferably within 4 hours. For example such markers include osteocalcin (also known as bone GLA protein of BGP), pro-peptides of procollagen type I, bone alkaline phosphatase and total alkaline phosphatase. Suitable methods for the determination of these markers can be found, for example, in Delmas, P. D., et al., J. Bone Min. Res. (1986) 1:333–337.

The assay of the present invention which provides an index to determination of the metabolic status of tissues, which generate collagen-derived peptides and isomerised and/or racemised peptide analogues when degradation occurs, is useful in a variety of contexts.

The assays may be used to assess an abnormal condition of a subject by indicating excessive bone resorption. This may show the presence of an osteoporotic condition or the metastatic progress of an malignancy. Other conditions characterised by excessive bone resorption include Paget's disease and hyperparathyroidism.

7. EXAMPLES

The working of the invention will be illustrated by the following examples.

7.1 Example 1

The present invention is in part based in part on the discovery that in serum there are collagen fragments which include an epitope present in the sequence EKAHDGGR or its above described variants and which have a molecular weight greater than that of fragments located previously in urine, indicating that such serum fragments will contain additional amino acid resi-dues against which a second antibody may be directed in a sandwich assay. The above mentioned collagen fragments discovered here are generated during bone resorption and their quantification can therefore be used for estimation of the rate of bone loss. This subpopulation of telopeptide fragments has not been measured previously.

The presence of these larger antigen fragments of collagen is demonstrated in this example.

Antigens reactive with a monoclonal antibody MabA7 raised against the non-isomerised L aspartate containing amino acid peptide sequence EKAHDGGR were affinity purified using the said antibody. Separate purification were carried out using serum and urine as the sources for such antigens.

200 µl of affinity purified urine antigen was applied at 4° C. to the Superdex(™) 75 HR column. Elution was achieved with a flow rate of approximately 0.3 ml/min., one ml fractions were collected, 15 µl of each fraction was transferred to the coated plate and assayed in the CrossLaps(™) urine ELISA.

The CrossLaps(™) assay employed was a polyclonal antibody serum based competition assay in which peptides of the sequence EKAHβDGGR are immobilised in the wells of a microtitre plate and compete for the antibody in the serum against collagen fragments in the sample.

Serum antigens were analysed in a similar manner.

Human urine antigens appeared to elute in a well defined (narrow) peak around 17 ml. The corresponding serum antigens (affinity purified by 6E-sepharose) eluted just before at 16 ml but in a broader peak (13–18 ml).

These results indicate that the molecular weight of the urine antigens is more homogeneous and that serum contains a population of antigens having a molecular weight higher than those in urine. These serum antigens are further studied in the following example.

7.2. Example 2

90 ml human serum (HS) from a healthy 24 year old male donor was mixed on a whirlmixer and divided into 18 equally sized pools of 5 ml each. Three portions were kept at 4° C. until ELISA measurement. The last 15 portions were extensively dialysed against PBS for four days at 4° C. in Spectrum(™) dialysis tubing (DispoDialyzer(™)).

Three portions were dialysed in tubing with a molecular weight cut off (MWCO) of 1000 Da, three portions were dialysed in tubing with a MWCO of 3500 Da, three portions were dialysed in tubing with a MWCO of 5000, three portions were dialysed in tubing with a MWCO of 10000 and three portions were dialysed in tubing with a MWCO of 25000. Serum samples were weighed prior to an after dialysis in order to determine possible changes in sample volume. Finally all portions were assayed in the two serum ELISAs (α-CLS, β-CLS) in order to determine the antigen recovery in the retentate. The α-CLS assay measure fragments containing the normal peptide EKAHDGGR whilst the β-CLS assay is specific for fragments containing the isomerised form.

The CrossLaps(™) serum (β-CLS) antigenicity was not decreased significantly (decrease less than 5 percent) in the retentate after dialysis in tubing with a MWCO of 1000 Da, indicating that most of all β-CLS antigens have a molecular weight above 1 kDa and that no antigen is "lost" by adhesion to the dialysis membrane. In contrast more than fifty percent of the β-CLS antigenicity was lost after dialysis in tubing with a MWCO of 3500 Da, indicating that at least half of the β-CLS immunoreactive molecules in HS have a molecular weight below 3500 Da. Sixty percent of the β-CLS antigenicity was lost after dialysis in tubing with a MWCO of 5000 Da, and more than 70 percent was lost in tubing with a MWCO of 10000 Da. 80 percent of the β-CLS antigenicity was lost with MWCO of 25000 Da indicating that subpopulation (20%) of the CrossLaps(™) serum antigens are high molecular moieties. Likewise some α-CLS antigenicity (approximately 10–15%) remained even in tubing with MWCO of 25000 Da, indicating the presence of high molecular weight α-CLS antigens. However, more than 70 percent of the α-CLS antigenicity was lost by dialysis in tubing with MWCO of 5000 Da showing that at least 70 percent of the α-CLS antigens are low molecular moieties (<5 kDa).

Previous investigations have shown that the molecular weight of collagen fragments in urine reactive in the CrossLaps(™) assay is about 2000 Daltons.

7.3. Example 3

7.3.1. Preparation of EKAH-βD-GGR Specific Monoclonal Antibodies

Two monoclonal antibody producing cell lines were separately obtained by the following procedures.

Female Balb/C*CF1 mice (8–12 weeks of age) were immunised intraperitoneally with 200 µl of an emulsion of complete Fruend's adjuvant and EKAH-βD-GGR conjugated to thyroglobulin (100 mg/L) by a carboiimide procedure. The conjugate and the adjuvant was mixed in equal volumes. Immunisations were repeated six times every 2 weeks using incomplete Freund's adjuvant. Three days prior to fusion the mice were boosted intraperitoneally with 100 µL EKAH-βD-GGR conjugated to thyroglobulin. Spleen cells and ATCC P3-X63-Ag8.653 (Kearney et al., J. Immunol 123:1548–50(1979)) myeloma cells were fused with 50% polyethylene glycol (PEG 4000 GK) as previously described expect that human endothelial culture supernatant (HECS, Costar, The Netherlands) was used instead of feeder cells (Astaldi et al., J. Immunol 25:1411-1 (1980)).

7.3.2. Screening of Monoclonal Antibodies

Hybridoma supernatants were diluted in assay buffer (300 mmol/l TRIS, 10 g/l bovine serum albumin, 5 g/l Tween 20; pH=8.0) and incubated in microtitre wells (Nunc, Kamstrup, Denmark) coated with either EKAH-βD-GGR conjugated to BSA by glutaraldehyde procedure or non-conjugated collagenase treated collagen (CTC) from human bone. Binding of antibodies was then detected using peroxidase conjugated rabbit anti-mouse 1 gG (DAKO A/S, Glostrup, Denmark). Hybridomas producing antibodies binding to EKAH-βD-GGR and CTC were cloned, propagated and the monoclonal antibodies were purified using Protein-A chromatography (Pharmacia, Uppsala, Sweden). Two monoclonal antibodies from two different fusions were selected, and they were designated F1103 and F12, respectively. The specificity studies of these two monoclonal antibodies revealed that they had similar reactivity towards the β-isomerised form of EKAHDGGR.

7.4. Example 4

7.4.1. Biotinylation of F1103 and Coupling to Horse Radish Peroxidase of F12

149 µl of Biotinamidocaproate-N-hydroxysuccimide ester (BxNHS) (0.59), dissolved in dimethylsulfoxide (DMSO) (4 mg/ml) is added to 5000 µl of a solution of Protein-A purified monoclonal antibody F1103 (2.0 mg/ml, prepared in PBS buffer (10 mg). Then 550 µl of 1 mol/l NaCO3/NaHCO3; pH=9.6 is added to give a final concentration of 0.1 mol/l, for adjustment of pH. The weight ratio between antibody and BxNHS is 16:1. The mixture is incubated at room temperature for 2 hours on end-over-end rotation (12 rpm). The reaction is stopped by the addition of 900 µl of 0.2 mol/l ethanolamine (1.5 ml/mg BxNHS) and incubated for 1 hour at room temperature. PBS buffer (15 ml) is added. The preparation is dialysed (cut-off value: 12.000–14.000) against 2*5 liter PBS buffer for 2 days at 4° C. Turbidity is removed by sterile filtration using 0.22 µm disposable syringe filter holder (Minisart NML, Sartorius). Coupling to horseradish peroxidase is carried out by the method of Nakane and Kawaoi (1974) J. Histochem. Cytochem. 22,1084. The conjugate is stored at −20° C.

7.5. Example 5

7.5.1. Sandwich Assay Procedures

Calibrators, controls and unknown samples (serum or plasma) are pipetted into microtitre wells coated with streptavidin followed by a mixture of a biotinylated antibody and a peroxidase conjugated antibody. Then, a complex between analyte in the specimen, biotinylated antibody and peroxidase-conjugated antibody is generated and bound to the streptavidin surface via the biotin conjugate. Following the one-step incubation at room temperature the wells are emptied and washed. A chromogenic substrate is added and colour reaction is then stopped with sulphuric acid and measured at 450 nm.

All solutions are equilibrated to room temperature (18–25° C.) prior to use.

Before starting the determination the biotinylated antibody and the peroxidase-conjugated antibody are diluted into an Assay Buffer (50 mM phosphate, 150 mM NaCL, 1% BSA, 0.1% Tween 20; pH=7.0). 50 µl of either Calibrators, Control or unknown samples are pipetted into streptavidin coated microtitre wells followed by 100 µl of the Antibody Solution. The mixture is incubated for 120 minutes at room temperature. The microwells are washed with 20 mM TRIS, 80 mM NaCl; pH=7.5. 100 µl of chromogenic substrate solution (ex TMB or ATBS<R>0) are pipetted into each microwell. The substrate solution is incubated for 15 minutes and stopped with 100 μl 0.18 mol/l sulphuric acid. The absorbance at 450 nm is measured.

The above procedure was followed using biotinylated antibody F1103 and peroxidase coupled antibody POD-F12. This assay is referred to in the accompanying Figures of the drawings as the "One-step CrossLaps (or ββXL) ELISA". As the sample, fractions from HMC of urine were used containing respectively one of the isomeric forms of the crosslink fragment of Formula 1, in which the peptide or peptide analogue chains are (1) both α bonded at D, (2) one α and one β, or (3) both β.

The assay showed essentially no capability of responding to either α, α or α,β forms but responded to the β,β form of the compound of Formula 1 in a sample-concentration dependent manner.

Figure 1:
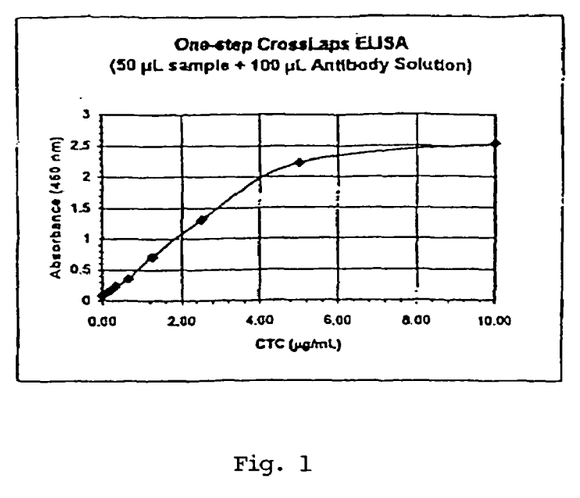
FIG. 1 shows a calibration curve obtained in Example 5.

A calibration curve obtained using collagenase treated collagen solution (CTC) as a calibration is shown in FIG. 1 and results of testing samples containing the three isomers of Formula 1 at two dilutions are shown in Table 1 below.

TABLE 1

| Sample Formula 1 | Dilution (PBS) | OD450 | μg/ml |
|---|---|---|---|
| α, α | 1:1 | 0.140 | 0.01 |
|  | 1:2 | 0.108 | 0.00 |
| α, β | 1:1 | 0.113 | 0.00 |
|  | 1:2 | 0.098 | 0.00 |
| β, β | 1:1 | 2,912 | >6.00 |
|  | 1:2 | 1,102 | 1.23 |

7.6. Example 6

Urine samples from post-menopausal women taken prior to treatment and after nine months bisphosphonate treatment were measured according to the method of Example 5 (β-β ELISA) and by a known assay (CrossLaps(™)) which is a competition assay based on a polyclonal serum recognising the β isomeric form of the amino acid sequence EKAHDGGR.

Figure 2:
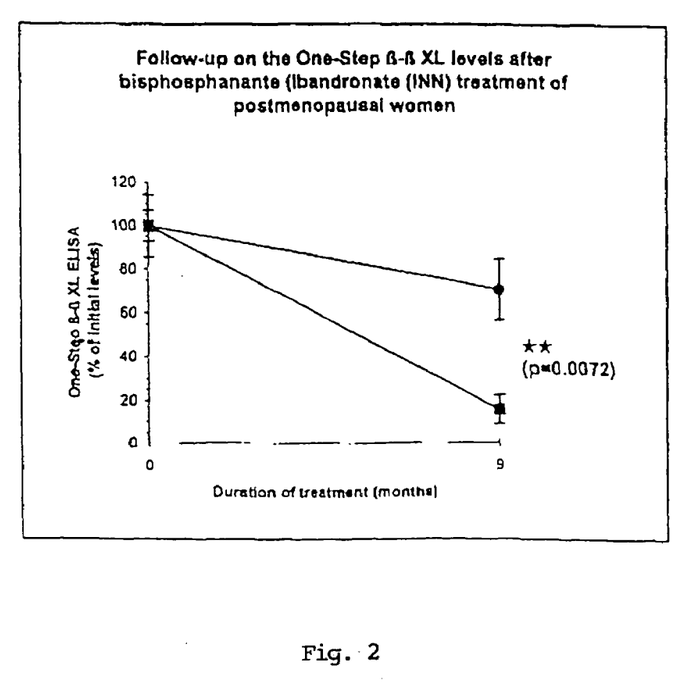
FIG. 2 shows the results measured according to the invention in Example 6.
Figure 3:
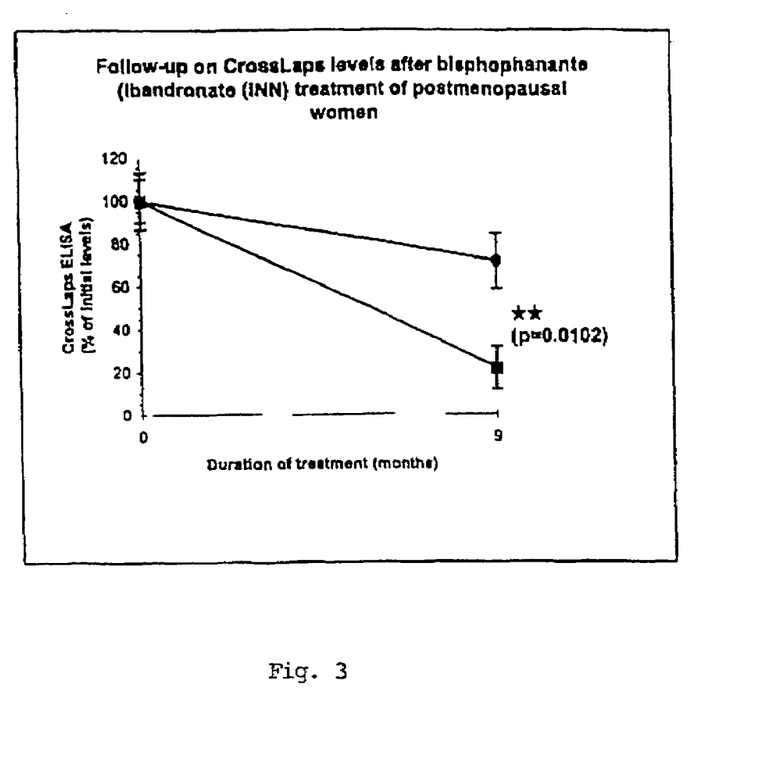
FIG. 3 shows the comparative data obtained in Example 6.

The results are shown in FIGS. 2 and 3. It can be seen that the ELISA according to the invention successfully follows the effect of treatment on reducing bone resorption.

7.7. Example 7

Sandwich assay for C-telopeptides of type II collagen using the same monoclonal antibody on either side of the sandwich.

Monoclonal antibodies to C-telopeptides of type II collagen were prepared as described for antibodies to C-telopetides of type I collagen (U.S. Pat. No. 09/319,539), except that the type II collagen specific sequence EKGPDP was used for immunisation and screening in stead of the type I collagen specific sequence EKAHDGGR. One purified monoclonal antibody, F4601, specific for the sequence EKGPDP was biotinylated and labelled with horseradish peroxidase as described below.

Biotinylation was performed by mixing 1 ml of F46 in PBS (1 mg/ml) with 110 μL 1M NaCO3/NaHCO3, pH 9.6, and subsequently adding 8 μL of biotinamidocaproate-N-hydroxysuccinimide ester (SIGMA) in DMSO (10 mg/110 μL DMSO). The reaction mixture was incubated end-over-end for one hour and dialysed extensively against PBS. Peroxidase-labelling was performed using a Peroxidase Labelling Kit from Roche Diagnostics (Cat. No. 1 829 696), and following the instructions of the manufacturer.

A sandwich ELISA was developed for measurement of C-telopeptides of type II collagen in human urine. Briefly, human urine was diluted in a PBS buffer containing 1% BSA XX (PBS-BTB) and 25 μL was added in duplicate to wells of microtitre plates coated with streptavidin (Roche Diagnostics GmbH). Biotinylated F46 and peroxidase-labelled F46 were diluted in PBS-BTB at concentrations of 500 and 1000 ng/ml, respectively, mixed 1+1 and 100 μl of the antibody mixture added to each well of the microtitre plate. After one hour of incubation at room temperature with shaking, the wells were washed 5 times and subsequently incubated with 100 μL of a chromogenic substrate solution (TMB, Kem-En-Tec, Denmark). The plates were incubated for 15 minutes in the dark and the colour reaction was stopped by addition of 100 μL 0.18M sulphuric acid. The absorbance was read at 450 nm with 650 nm as reference.

Figure 4:
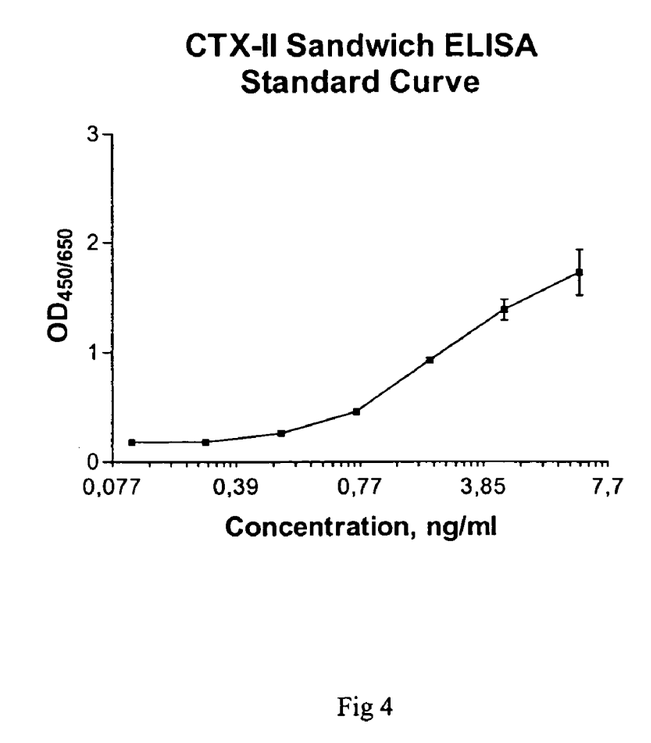
FIG. 4 shows the results of a sandwich ELISA assay for C-telopeptides of type II collagen.

In FIG. 4 it is demonstrated that a standard curve can be generated by dilution of a human urine specimen and measuring the samples in the sandwich ELISA described above. This indicates that C-telopeptides of type II collagen in human urine can be detected using the same monoclonal antibody on either side of the sandwich ELISA.

Fragments detectable in this way may include collagen type II derived fragments of the formula:

and larger fragments containing this moiety. The presence and amount of collagen type II fragments, including these, can be related to the presence and intensity of disease conditions involving resorption of cartilage, e.g. osteoarthritis and rheumatoid arthritis or other inflammatory joint conditions.

The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

What is claimed is:

1. A method of measuring the amount of the rate of type II collagen resorption comprising measuring in a sample the amount of a population of collagen type II fragments by a sandwich assay comprising forming antibody-fragment-antibody complexes involving a first antibody specifically reactive with first occurrence in said fragments of an epitope located in or comprised by part of the collagen type II amino acid sequence and a second antibody specifically reactive with a second occurrence or said epitope in said fragments by reacting each antibody with said fragments, measuring the amount of said complexes formed and correlating said measured amount with the rate of type II collagen resorption, wherein said part of the collagen type II amino acid sequence is EKGPDP.

2. The method as claimed in claim 1, wherein the measured amount of said complexes is compared with calibration values correlating said amount to a clinical condition.

3. The method as claimed in claim 2, wherein said clinical condition is cartilage resorption, osteoarthritis, rheumatoid arthritis or other inflammatory joint disease.

4. The method as claimed in claim 1, wherein the same antibody is used as said first antibody and as said second antibody.

* * * * *

SEQUENCE LISTING

<160> NUMBER OF SEQ ID NOS: 7

<210> SEQ ID NO 1
<211> LENGTH: 8
<212> TYPE: PRT
<213> ORGANISM: Homo sapiens

```
<400> SEQUENCE: 1

Glu Lys Ala His Asp Gly Gly Arg
 1               5

<210> SEQ ID NO 2
<211> LENGTH: 7
<212> TYPE: PRT
<213> ORGANISM: Homo sapiens

<400> SEQUENCE: 2

Phe Asp Phe Ser Phe Leu Pro
 1               5

<210> SEQ ID NO 3
<211> LENGTH: 11
<212> TYPE: PRT
<213> ORGANISM: Homo sapiens

<400> SEQUENCE: 3

Pro Pro Gln Glu Lys Ala His Asp Gly Gly Arg
 1               5                  10

<210> SEQ ID NO 4
<211> LENGTH: 8
<212> TYPE: PRT
<213> ORGANISM: Homo sapiens

<400> SEQUENCE: 4

Gly Met Lys Gly His Arg Gly Phe
 1               5

<210> SEQ ID NO 5
<211> LENGTH: 8
<212> TYPE: PRT
<213> ORGANISM: Homo sapiens
<220> FEATURE:
<221> NAME/KEY: MOD_RES
<222> LOCATION: (5)
<223> OTHER INFORMATION: D aspartic acid

<400> SEQUENCE: 5

Glu Lys Ala His Xaa Gly Gly Arg
 1               5

<210> SEQ ID NO 6
<211> LENGTH: 16
<212> TYPE: PRT
<213> ORGANISM: Homo sapiens

<400> SEQUENCE: 6

Cys Ser Ala Gly Phe Asp Phe Ser Phe Leu Pro Gln Pro Pro Gln Glu
 1               5                  10                  15

<210> SEQ ID NO 7
<211> LENGTH: 6
<212> TYPE: PRT
<213> ORGANISM: Homo sapiens

<400> SEQUENCE: 7

Ala His Asp Gly Gly Arg
 1               5
```